(12) United States Patent
Saito et al.

(10) Patent No.: US 8,982,202 B2
(45) Date of Patent: Mar. 17, 2015

(54) IMAGE PICKUP SYSTEM

(71) Applicant: Olympus Medical Systems Corp., Tokyo (JP)

(72) Inventors: Saeri Saito, Sagamihara (JP); Jun Konishi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/915,215

(22) Filed: Jun. 11, 2013

(65) Prior Publication Data

US 2013/0329028 A1 Dec. 12, 2013

Related U.S. Application Data

(63) Continuation of application No. PCT/JP2012/083451, filed on Dec. 25, 2012.

(30) Foreign Application Priority Data

Mar. 1, 2012 (JP) .................................. 2012-045823

(51) Int. Cl.
| | |
|---|---|
| A61B 1/04 | (2006.01) |
| H04N 7/18 | (2006.01) |
| A61B 1/00 | (2006.01) |
| A61B 1/045 | (2006.01) |

(52) U.S. Cl.
CPC .............. *H04N 7/18* (2013.01); *A61B 1/00006* (2013.01); *A61B 1/045* (2013.01)

USPC ............................................................ 348/68

(58) Field of Classification Search
CPC ....... A61B 1/00006; A61B 1/045; H04N 7/18
See application file for complete search history.

(56) References Cited

U.S. PATENT DOCUMENTS

| | | | |
|---|---|---|---|
| 6,456,875 B1 * | 9/2002 | Wilkinson et al. ................. | 607/2 |
| 6,638,212 B1 | 10/2003 | Oshima | |
| 2003/0134591 A1 * | 7/2003 | Roberts et al. ............... | 455/3.06 |
| 2008/0108870 A1 * | 5/2008 | Wiita et al. ................... | 600/112 |
| 2009/0216080 A1 | 8/2009 | Nakamura et al. | |

FOREIGN PATENT DOCUMENTS

| | | |
|---|---|---|
| EP | 2 094 002 A2 | 8/2009 |
| JP | 2008-149125 A | 7/2008 |
| JP | 2009-195602 A | 9/2009 |
| JP | 2011-147548 A | 8/2011 |

* cited by examiner

*Primary Examiner* — Sath V Perungavoor
*Assistant Examiner* — Peter D Le
(74) *Attorney, Agent, or Firm* — Scully, Scott, Murphy & Presser, PC

(57) ABSTRACT

An image pickup system is an image pickup system in which an image pickup device arranged at a distal end of an insertion section of an endoscope and a processor can communicate with each other. A group of multiple control parameters to be collectively transmitted and checksum codes related to the parameters are transmitted from the processor to the image pickup device, and the image pickup device reflects the control parameters on a register only when all the received multiple control parameters are normal, on the basis of the checksums.

12 Claims, 9 Drawing Sheets

(A)

○ STARTING POINT
● ENDING POINT (B)

| GAIN SETTING | ELECTRONIC SHUTTER SETTING | BINNING SETTING | CHECKSUM OF ALL FUNCTIONS |
|---|---|---|---|

FIG.5

| CHECKSUM OF GAIN | ELECTRONIC SHUTTER SETTING | CHECKSUM OF ELECTRONIC SHUTTER | BINNING SETTING | CHECKSUM OF BINNING |
|---|---|---|---|---|

FIG.6

| GAIN SETTING | ELECTRONIC SHUTTER SETTING | BINNING SETTING | CHECKSUM OF GAIN | CHECKSUM OF ELECTRONIC SHUTTER | CHECKSUM OF BINNING |
|---|---|---|---|---|---|

IMAGE PICKUP SYSTEM

CROSS REFERENCE TO RELATED APPLICATION

This application is a continuation application of PCT/JP2012/083451 filed on Dec. 25, 2012 and claims benefit of Japanese Application No. 2012-045823 filed in Japan on Mar. 1, 2012, the entire contents of which are incorporated herein by this reference.

BACKGROUND OF THE INVENTION

1. Field of the Invention

The present invention relates to an image pickup system which includes an endoscope provided with an image pickup device arranged at a distal end of the endoscope.

2. Description of the Related Art

Recently, endoscopes provided with an image pickup device have been widely used in a medical field and an industrial field.

A technique is also known in which various signal processings related to an endoscope are performed by a signal processing apparatus referred to as a processor, which is removably connected to the endoscope.

Furthermore, in this kind of endoscope, it is necessary to, at the image pickup device arranged at a distal end side of an insertion section, acquire multiple control parameters for controlling the image pickup device at the time of or after startup and appropriately make register settings. Note that, as the register settings, an example given in Japanese Patent Application Laid-Open Publication No. 2011-147548 is known.

The multiple control parameters are sent out from a control section configured, for example, by an FPGA. In this kind of endoscope, the control section and the like are arranged in an operation section of the endoscope, a connector connecting the endoscope and the processor, or in the processor itself because of space limitations that can be secured around the image pickup device.

SUMMARY OF THE INVENTION

An image pickup system of an aspect of the present invention is an image pickup system comprising an image pickup apparatus generating and outputting an image signal by receiving a light and performing photoelectric conversion, and a control apparatus sending out control parameters for performing drive control of the image pickup apparatus, the image pickup apparatus and the control apparatus being capable of communicating with each other, and the image pickup system comprising: a first communication section being provided in the control apparatus and transmitting multiple control parameters for controlling photographing of the image pickup apparatus to the image pickup apparatus; a second communication section being provided in the image pickup apparatus and receiving the control parameters transmitted from the first communication section; a judgment section being provided in the control apparatus and judging whether the multiple control parameters received by the second communication section are normal or not; a control-apparatus-side control section being provided in the control apparatus and transmitting, when judging that the multiple control parameters received by the image pickup apparatus are normal on the basis of a result of the judgment by the judgment section, a control signal permitting the image pickup apparatus to reflect the multiple control parameters related to the judgment result, to the image pickup apparatus via the first communication section; and a photographing control section being provided in the image pickup apparatus and being for performing photographing control by the multiple control parameters received by the second communication section, on the basis of the result of the judgment by the judgment section.

BRIEF DESCRIPTION OF THE DRAWINGS

FIG. 4 is a diagram illustrating an example of communicated contents of the control parameters and an error detecting code transmitted in the image pickup system of the first embodiment;

FIG. 5 is a diagram illustrating an example of communicated contents of control parameters and error detecting codes transmitted in an image pickup system of a second embodiment of the present invention;

FIG. 6 is a diagram illustrating an example of communicated contents of control parameters and error detecting codes transmitted in an image pickup system of a third embodiment of the present invention;

DETAILED DESCRIPTION OF THE PREFERRED EMBODIMENTS

Embodiments of the present invention will be described in detail below with reference to drawings.

First Embodiment

Figure 1:
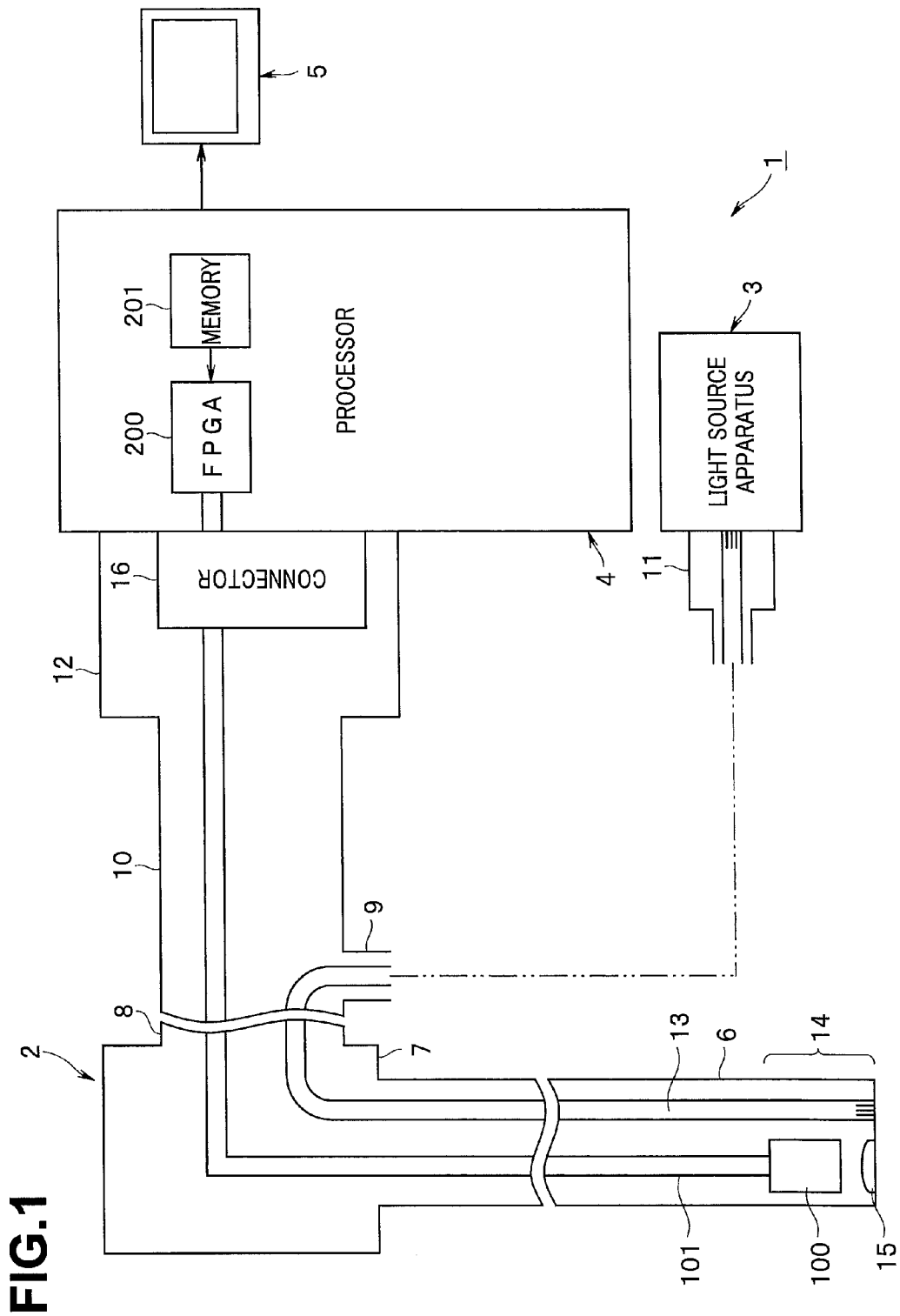
FIG. 1 is a diagram showing a whole configuration of an image pickup system of a first embodiment of the present invention.

As shown in FIG. 1, an image pickup system 1 provided with an image pickup apparatus according to a first embodiment of the present invention is provided with: an endoscope 2 provided with an image pickup device 100, a light source apparatus 3 to which the endoscope 2 is removably connected and which supplies an illumination light to the endoscope 2, a processor 4 as a signal processing apparatus to which the endoscope 2 is removably connected and which performs predetermined signal processing, and a monitor 5 as a display apparatus which displays an image signal generated by the processor 4 as an endoscopic image.

The endoscope 2 has an elongated insertion section 6 to be inserted into a body cavity, an operation section 7 provided at a rear end of the insertion section 6, and a universal cord 8 extended from the operation section 7. The universal cord 8 branches into a light guide cord 9 and a signal cord (signal cable) 10 near a proximal end thereof or midway. A light source connector 11 at an end of the light guide cord 9 is removably connected to the light source apparatus 3, and a signal connector 12 at an end of the signal cord 10 is removably connected to the processor 4.

A light guide 13 for transmitting an illumination light is inserted through the insertion section 6, the operation section 7 and the universal cord 8. By connecting the light source connector 11 to the light source apparatus 3, an illumination light from the light source apparatus 3 is transmitted to the light guide 13, and the transmitted illumination light is emitted from a light guide distal end surface attached to an illumination window provided at a distal end portion 14 of the insertion section 6. Note that such a configuration is also possible that a connector in which the light source connector 11 and the signal connector 12 are integrated is connected to the light source apparatus 3 so that a signal of the signal connector 12 may be handed over from or to the processor 4 via a cable connecting the light source apparatus 3 and the processor 4.

The distal end portion 14 is provided with an observation window (image pickup window) adjacent to the illumination window, and an objective lens 15 which forms an optical image of an object, such as an illuminated affected part, is attached to the observation window. At an image forming position of the objective lens 15, an image pickup device configured, for example, by a CMOS image sensor (hereinafter briefly referred to as a CIS) 100 is arranged.

The CIS 100 is connected to a connector 16 provided inside the signal connector 12 via an integrated coaxial cable 101 inserted through the insertion section 6 and the universal cord 8, and the connector 16 is removably connected to the processor 4.

The processor 4 is provided with: a power supply circuit not shown which generates power supplies with multiple power supply voltages required for operations of the image pickup device and the like, a signal processing circuit (not shown in FIG. 1) which performs predetermined signal processing for an image pickup signal outputted from the image pickup device and a control circuit (not shown in FIG. 1) which performs control, including the power supply circuit and the signal processing circuit, as well as a control section (FPGA) 200 for transmitting multiple control parameters for controlling the CIS 100 to the CIS 100, which is configured, for example, by an FPGA, and a memory 201 which stores information about the multiple control parameters. Note that other components in the processor 4 will be described in detail later.

In the present embodiment, the control section (FPGA) 200 is adapted to read out various setting values of the multiple control parameters from the memory 201 and transmit the setting values to the CIS 100 via the integrated coaxial cable 101 by communication. Note that transmission operation of the multiple control parameters will be described later.

The control section 200 is configured by an FPGA in the present embodiment but is not limited thereto. Other communication devices are also possible.

The integrated coaxial cable 101 extends from an output end of the CIS 100 into the insertion section 6, further passes through the universal cord 8, and is removably connected to the processor 4 via the connector 16 provided inside the signal connector 12.

The integrated coaxial cable 101 is a cable which connects the CIS 100 and the processor 4 and through which not only power supply to the CIS 100 is transmitted but also a video signal (a serial signal) on which a synchronization signal transmitted from the CIS 100 is superimposed, a vertical synchronization signal (VD) transmitted from the processor 4, communicated contents of multiple control parameters, and an error correcting code or an error detecting code transmitted from the processor 4 to the CIS 100, and the like are transmitted and received.

The integrated coaxial cable 101 is shielded with a shield member formed by an exterior member of the insertion section 6. Furthermore, the shield member is electrically connected to a shield member formed by an exterior member of the operation section 7, a shield member formed by an exterior member of the universal cord 8, a shield member of the signal connector 12 and the like.

Figure 2:
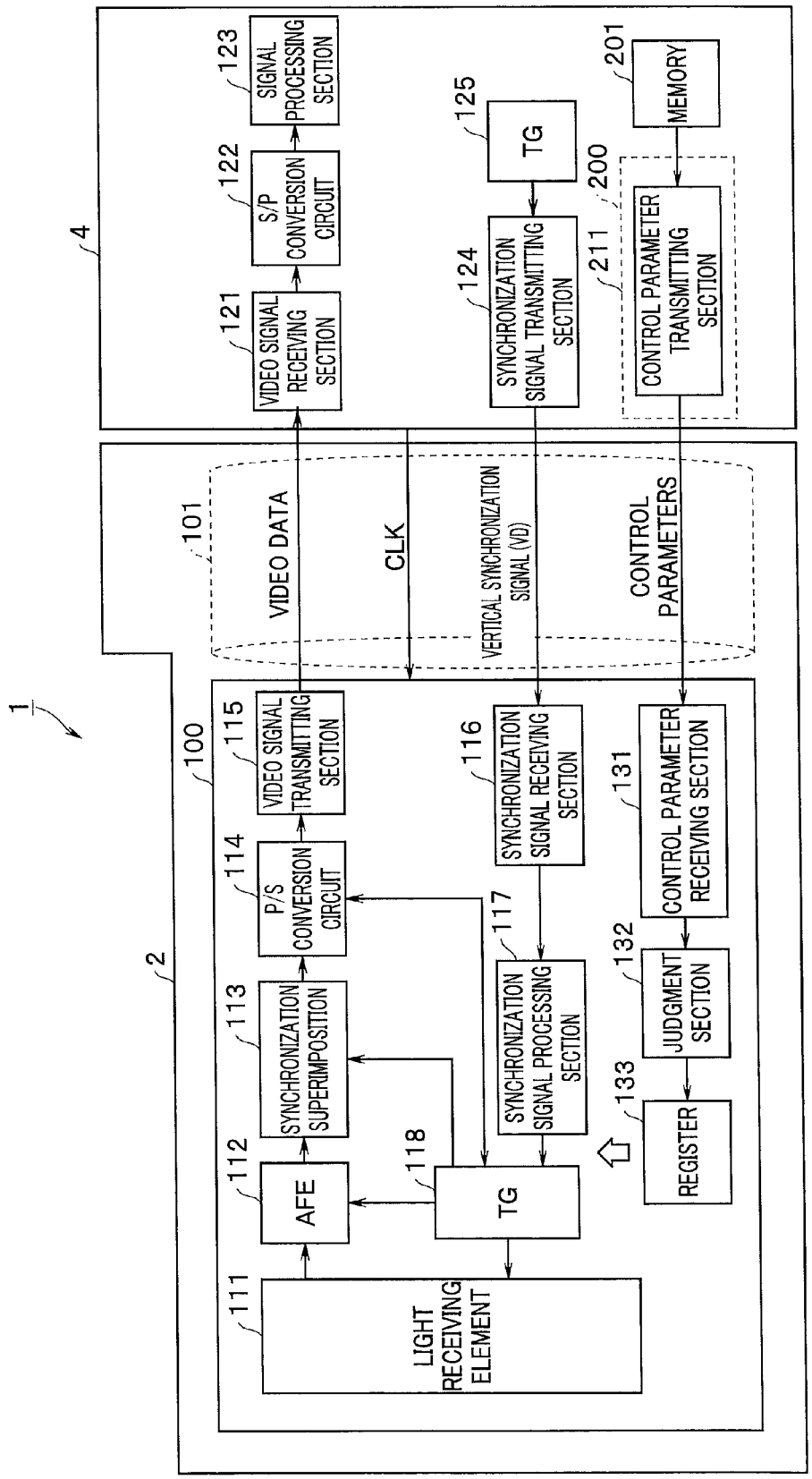
FIG. 2 is a diagram showing a configuration of an electric system in the image pickup system of the first embodiment.

FIG. 2 is a block diagram showing a configuration of an electric system in the image pickup system of the present embodiment.

The image pickup device (CIS) 100 is configured by a so-called CMOS (complementary metal oxide semiconductor circuit) image sensor and is configured being provided with: a light receiving element 111 arranged at the image forming position of the objective lens 15, an AFE (analog front end) 112 which removes noise from a signal outputted from the light receiving element 111 and digitizes the signal, a synchronization superimposition circuit 113 which superimposes a synchronization signal on a video signal, which is an output signal of the AFE 112, a P/S conversion circuit 114 for converting the video signal to a serial signal for transmission to output the serial signal to an outside, a video signal transmitting section 115 for outputting the video signal (serial signal) to the outside, a synchronization signal receiving section 116 which receives a vertical synchronization signal (VD) and the like from the outside, for example, from the processor 4, a synchronization signal processing section 117 which performs predetermined processing for the synchronization signal from the outside received by the signal receiving section 116 (the vertical synchronization signal (VD) received from the processor 4) in a predetermined case, and a timing generator (TG) 118 which generates its own synchronization signal in the CIS 100 and causing its own synchronization signal to follow the external synchronization signal for which the predetermined processing has been performed by the synchronization signal processing section 117 to supply the synchronization signal to respective circuits as various synchronization signals in the CIS 100 as well as a control parameter receiving section 131 which receives control parameters, and an error correcting code or an error detecting code transmitted from the control section (FPGA) 200, a judgment section 132 which judges whether or not the received control parameters have been correctly transmitted and received, on the basis of the error correcting code or the error detecting code (in the present embodiment, a checksum code) added to communicated contents of the control parameters received by the control parameter receiving section 131, and a register 133 which stores control parameters and the like to be used for photographing control in the CIS 100.

On the other hand, the processor 4 is provided with: a video signal receiving section 121 which receives a video signal (serial signal) having video data transmitted from the CIS 100, an S/P conversion circuit 122 which converts the video signal (serial signal) with a synchronization signal superimposed thereon, which has been received by the video signal receiving section 121, to a parallel signal, a signal processing section 123 which performs predetermined signal processing for the received video signal and outputs the video signal to the monitor 5 and the like, a timing generator (TG) 125 which generates a vertical synchronization signal (VD) for image processing in the processor 4 and supplies the vertical synchronization signal (VD) to various circuits, a synchronization signal transmitting section 124 which transmits the vertical synchronization signal (VD) in the processor 4 supplied from the timing generator (TG) 125 to the CIS 100, the above-described control section (FPGA) 200 which is configured, for example, by an FPGA, a control parameter transmitting section 211 for transmitting multiple control parameters for controlling the CIS 100 to the CIS 100, which is configured in the control section (FPGA) 200, and the memory 201 which stores information about the multiple control parameters.

Note that, though the control parameter transmitting section 211 is assumed to be configured in the control section (FPGA) 200 in the present embodiment, another component, the timing generator (TG) 125 may be configured in the FPGA.

In the present embodiment, the control section (FPGA) 200 reads out various setting values of the multiple control parameters from the memory 201 at the time of startup and transmits the setting values from the control parameter transmitting section 211 in the control section (FPGA) 200 to the CIS 100 via the integrated coaxial cable 101, for example, on the basis of an I2C interface. After the startup also, corresponding control parameters are transmitted via communication in order to change settings for a photographing mode, a gain setting, an electronic shutter setting, a cutout position and the like as necessary.

Though the I2C interface is adopted as a communication system in the present embodiment, the communication system is not limited thereto, and, another communication system, for example, an SPI interface may be adopted.

Next, multiple control parameters transmitted in the present embodiment will be described.

In the present embodiment, the control section (FPGA) 200 is adapted to read out various setting values of multiple control parameters from the memory 201 and transmit the setting values to the CIS 100 via the integrated coaxial cable 101 as described above. The "multiple control parameters" are classified into some groups. Multiple control parameters belonging to each group do not have a meaning until all the control parameters in the group are normally transmitted. That is, multiple control parameters belonging to a certain group are treated as a preset set of integrated information in the present embodiment.

The multiple control parameters transmitted in the image pickup system of the present embodiment are classified, for example, into following groups.

<Control Parameters: Group A>

Group A includes multiple control parameters for brightness (light adjustment), and, more specifically, the multiple control parameters are as follows:

(a) Gain (CDS gain, digital gain, AGC)
(b) Position of electronic shutter
(c) Binning setting (for example, a setting for addition of pixels, settings for how many pixels are to be added, the direction of the addition and the like)

There is a possibility that, if a part of these control parameters are reflected, unintentional inappropriate brightness control is performed. For example, since brightness changes as the number of added pixels changes, it is desirable to perform control of the binning setting simultaneously with control of the gain setting and the electronic shutter setting.

<Control Parameters: Group B>

Group B is a control parameter group for address information about a correction position, and, more specifically, two parameters of a parameter for x-coordinate data and a parameter for y-coordinate data correspond to Group B. Here, it is apparent that a correct operation is not performed even if only one control parameter is reflected. Both are to be accurately transmitted. Note that all address information is targeted.

<Control Parameters: Group C>

Group C is a control parameter group for specifying a predetermined "range" on a screen such as a cutout range. More specifically, there are various specification methods for specifying a cutout range, and, for example, a parameter for a cutout starting point position and a parameter for an ending point position correspond to Group C. Description will be made on a case where both of the parameter for a starting point position and the parameter for an ending point position are accurately transmitted and a case the parameters are not accurately transmitted, with the use of FIG. 3.

Figure 3:
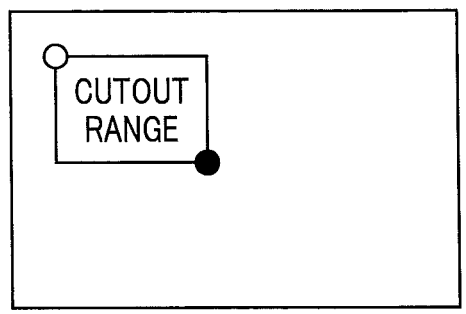
FIG. 3 is a diagram illustrating an example of control parameters transmitted in the image pickup system of the first embodiment.
Figure 3:
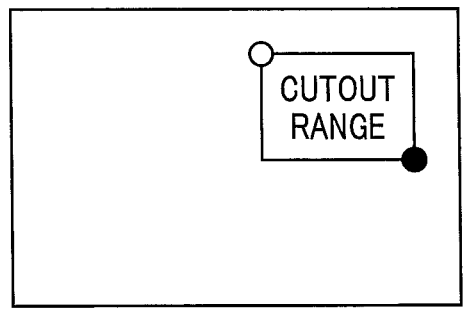
Figure 3:
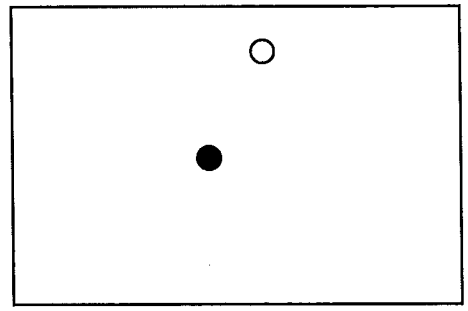

FIG. 3 is a diagram illustrating an example of transmission of a parameter specifying a cutout range among the multiple control parameters transmitted in the image pickup system of the first embodiment.

For example, in the case of changing a cutout range to a position shown in FIG. 3(B) in a state in which a starting point position and an ending point position shown in FIG. 3(A) are specified as an initial state of the cutout range, the position in FIG. 3(B) is reflected if both of the parameter for the starting point position and the parameter for the ending point position are accurately transmitted. However, for example, if the parameter for the starting point position is accurately transmitted but the parameter for the ending point position is not accurately transmitted, a relationship between the starting point position and the ending point position is in an abnormal state, and a cutout range does not exist, as shown in FIG. 3(C).

Note that, though the above three examples are given as the control parameter groups in the present embodiment, it goes without saying that the control parameter groups are not limited thereto, and the invention as claimed in the application concerned may be applied to another preset set of integrated information.

Next, operation in the present embodiment will be described.

In the present embodiment, an error correcting code (for example, a Hamming code or the like) or an error detecting code (a parity bit, a checksum or the like) is transmitted together with the communicated contents of the multiple control parameters described above.

That is, at the time of or after startup, the control section (FPGA) 200 reads out various setting values of multiple control parameters from the memory 201, in the processor 4, and transmits an error correcting code or an error detecting code (a parity bit, a checksum or the like) together with communicated contents of multiple control parameters from the control parameter transmitting section 211.

Description will be made below on an example of transmitting communicated contents of the multiple control parameters of Group A described above with a checksum code as the error detection code added thereto.

FIG. 4 is a diagram showing an example of transmitting communicated contents of control parameters about brightness (light adjustment) transmitted in the image pickup system of the first embodiment with a checksum code added thereto, and, more specifically, shows an example of transmitting a gain setting, an electronic shutter setting and a binning setting with a checksum code for all these functions added thereto.

The control parameter receiving section 131 in the CIS 100 receives communicated contents of a gain setting, an electronic shutter setting and a binning setting, and a checksum code for all these functions which are transmitted from the control parameter transmitting section 211 in the control section (FPGA) 200.

After that, the judgment section 132 judges whether or not the received control parameters have been correctly transmitted and received, on the basis of the checksum code added to the communicated contents of the control parameters received by the control parameter receiving section 131.

If the checksum result is OK as a result of the judgment by the judgment section 132, all of the gain setting, the electronic shutter setting and the binning setting are reflected on the register 133.

On the other hand, if the checksum result described above is NG as a result of the judgment by the judgment section 132, the judgment section 132 performs control so that none of the gain setting, the electronic shutter setting and the binning setting is reflected on the register 133. That is, if some setting value is already stored in the register 133, control is performed so that update with the newly received setting values is not performed.

Note that, though none of the new control parameter settings is reflected on the register 133 in the case of the checksum result being NG, in the present first embodiment as described above, content indicating that the checksum result is NG, that is, content indicating that the communication result is NG may be stored in another register not shown in the CIS 100 instead of or together with the above.

Otherwise, the content indicating that the communication result is NG may be notified to the control section (FPGA) 200 in the processor 4 via a signal line for transmitting a video signal from the CIS 100 or another signal line arranged in advance between the CIS 100 and the processor 4.

As described above, according to the first embodiment, it is possible to provide an image pickup system in which a CMOS image sensor is arranged at a distal end of an insertion section of an endoscope, and preset multiple control parameters required for photographing control are transmitted from a processor side to a CMOS image sensor side, the image pickup system being capable of always performing normal photographing control by treating the control parameters required for photographing control as a set of integrated information, and performing control so that information about the control parameters is reflected on a register in the CMOS image sensor only when all the multiple control parameters have been normally transmitted and contents of the register are not updated when all the multiple control parameters have not been normally transmitted.

Second Embodiment

Next, a second embodiment of the present invention will be described.

An image pickup system of the second embodiment of the present invention is configured similarly to the first embodiment. However, the communicated contents of the multiple control parameters, and the transmitted contents of the error correcting code or the error detecting code which are transmitted from a control parameter transmitting section 211 to a CIS 100 are different. Since the other components are equal to those of the first embodiment, detailed description thereof is omitted here.

FIG. 5 is a diagram showing an example of transmitting communicated contents of control parameters about brightness (light adjustment) transmitted in the image pickup system of the second embodiment with checksum codes added thereto, and, more specifically, shows an example of transmitting a gain setting, an electronic shutter setting and a binning setting with a checksum code added to each thereof.

In the second embodiment, a control parameter receiving section 131 in the CIS 100 receives communicated contents of a gain setting, an electronic shutter setting and a binning setting, and a checksum code combined with each thereof which are transmitted from the control parameter transmitting section 211 in a control section (FPGA) 200.

After that, a judgment section 132 judges whether or not the received multiple control parameters have been correctly transmitted and received, on the basis of the checksum codes of the respective control parameters added to the communicated contents of the control parameters received by the control parameter receiving section 131.

If all the checksum results are OK as a result of the judgment by the judgment section 132, all of the gain setting, the electronic shutter setting and the binning setting are reflected on a register 133.

On the other hand, if any of the respective checksum results is NG as a result of the judgment by the judgment section 132, the judgment section 132 performs control so that none of the gain setting, the electronic shutter setting and the binning setting is reflected on the register 133. In this case, if some setting value is already stored in the register 133, control is performed so that update with the newly received setting values is not performed, similarly to the first embodiment.

Note that, though none of the new control parameter settings is reflected on the register 133 in the case of any of the checksum results being NG in the present second embodiment also similarly to the first embodiment described above, content indicating that the checksum result is NG, that is, content indicating that the communication result is NG may be stored in another register not shown in the CIS 100 or the content indicating that the communication result is NG may be notified to the control section (FPGA) 200 in a processor 4 via a signal line for transmitting a video signal from the CIS 100 or another signal line arranged in advance between the CIS 100 and the processor 4, instead of or together with the above.

Note that, though FIG. 5 shows an example in which the gain setting, the electronic shutter setting and the binning setting combined with their respective checksum codes are continuously transmitted, the present embodiment is not limited thereto. Whether or not the multiple control parameters have been transmitted as a set of integrated information may be judged by specifying the number of kinds to be transmitted in a header in advance and detecting whether or not all the kinds of control parameters have been transmitted, by the control parameter receiving section 131 or the judgment section 132, which is a receiver.

As described above, according to the second embodiment, it is possible to provide an image pickup system in which a CMOS image sensor is arranged at a distal end of an insertion section of an endoscope, and preset multiple control parameters required for photographing control are transmitted from a processor side to a CMOS image sensor side, the image pickup system being capable of always performing normal photographing control by treating the control parameters required for photographing control as a set of integrated information, and performing control so that information about the control parameters is reflected on a register in the CMOS image sensor only when all the multiple control parameters have been normally transmitted and, for all the control parameters, contents of the register are not updated when any of the control parameters has not been normally transmitted, similarly to the first embodiment.

Third Embodiment

Next, a third embodiment of the present invention will be described.

An image pickup system of the third embodiment of the present invention is configured similarly to the first and second embodiments. However, the communicated contents of the multiple control parameters, and the transmitted contents of the error correcting code or the error detecting code which are transmitted from a control parameter transmitting section 211 to a CIS 100 are different from both of the first and second embodiments. Since the other components are equal to those of the first embodiment, detailed description thereof is omitted here.

FIG. 6 is a diagram showing an example of transmitting communicated contents of a control parameter about brightness (light adjustment) transmitted in the image pickup system of the third embodiment with checksum codes added thereto, and, more specifically, shows such an example that is similar to the second embodiment in that a gain setting, an electronic shutter setting and a binning setting are transmitted with a checksum code added to each thereof but that only the checksum codes are collected when being transmitted.

In the third embodiment also, a control parameter receiving section 131 in the CIS 100 receives communicated contents of a gain setting, an electronic shutter setting and a binning setting, and a checksum code combined with each thereof which are transmitted from a control parameter transmitting section 211 in a control section (FPGA) 200, similarly to the second embodiment.

After that, a judgment section 132 judges whether or not the received multiple control parameters have been correctly transmitted and received, on the basis of the checksum codes of the respective control parameters added to the communicated contents of the control parameters received by the control parameter receiving section 131.

If all the checksum results are OK as a result of the judgment by the judgment section 132, all of the gain setting, the electronic shutter setting and the binning setting are reflected on a register 133, similarly to the first and second embodiments.

On the other hand, if any of the respective checksum results is NG as a result of the judgment by the judgment section 132, the judgment section 132 performs control so that none of the gain setting, the electronic shutter setting and the binning setting is reflected on the register 133, similarly to the second embodiment. In this case, if some setting value is already stored in the register 133, control is performed so that update with the newly received setting values is not performed, similarly to the first and second embodiments.

In the present third embodiment also, content indicating that the checksum result is NG, that is, contents that a communication result is NG may be stored in another register not shown in the CIS 100, or the content that the communication result is NG may be notified to the control section (FPGA) 200 in a processor 4 via a signal line for transmitting a video signal from the CIS 100 or another signal line arranged in advance between the CIS 100 and the processor 4, similarly to the first and second embodiments described above.

As described above, according to the third embodiment, it is possible to provide an image pickup system in which a CMOS image sensor is arranged at a distal end of an insertion section of an endoscope, and preset multiple control parameters required for photographing control are transmitted from a processor side to a CMOS image sensor side, the image pickup system being capable of always performing normal photographing control by treating the control parameters required for photographing control as a set of integrated information, and performing control so that information about the control parameters is reflected on a register in the CMOS image sensor only when all the multiple control parameters have been normally transmitted and, for all the control parameters, contents of the register are not updated when any of the control parameters has not been normally transmitted, similarly to the second embodiment.

Fourth Embodiment

Next, a fourth embodiment of the present invention will be described.

The image pickup system of the first embodiment described above performs the judgment about whether multiple control parameters transmitted from a processor 4 side to a CIS 100 side have been normally transmitted or not by the CIS 100. In comparison, an image pickup system of the fourth embodiment of the present invention is characterized in performing the judgment on a processor 4A side.

Note that only such parts that are different from the first embodiment will be described here, and description of components similar to those of the first embodiments is omitted.

Figure 7:
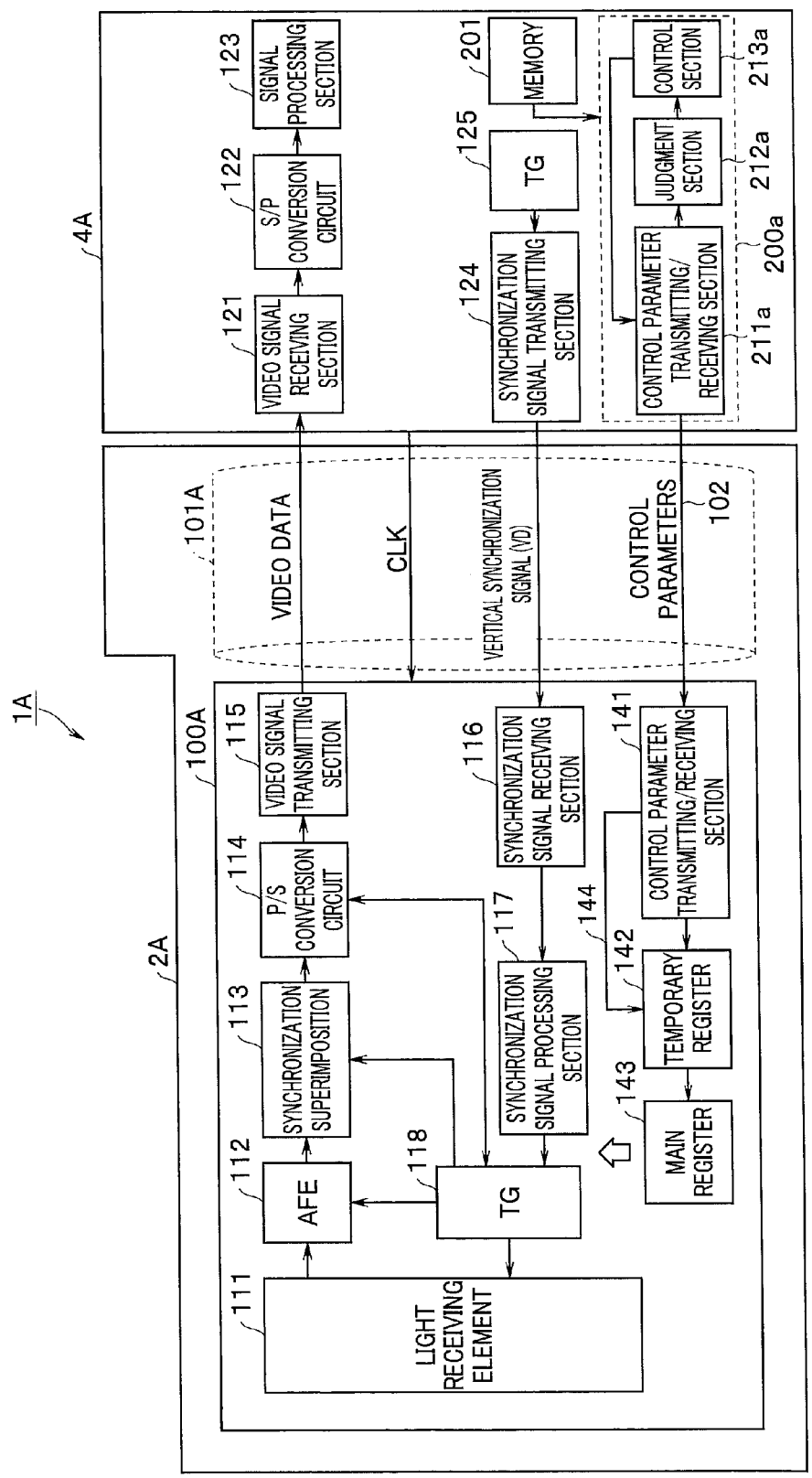
FIG. 7 is a diagram showing a configuration of an electric system in an image pickup system of a fourth embodiment of the present invention.

FIG. 7 is a block diagram showing a configuration of an electric system in the image pickup system of the fourth embodiment of the present invention.

As shown in FIG. 7, an image pickup system 1A provided with an image pickup apparatus according to the fourth embodiment of the present invention is provided with: an endoscope 2A provided with an image pickup device (CIS) 100A, a light source apparatus to which the endoscope 2A is removably connected and which supplies an illumination light to the endoscope 2A, a processor 4A as a signal processing apparatus to which the endoscope 2A is removably connected and which performs predetermined signal processing, and a monitor as a display apparatus which displays an image signal generated by the processor 4A as an endoscopic image.

Similarly to the first embodiment, the image pickup device (CIS) 100A in the image pickup system 1A of the fourth embodiment is configured by a so-called CMOS (complementary metal oxide semiconductor circuit) image sensor arranged at a distal end of an insertion section and connected to the processor 4A via an integrated coaxial cable 101A inserted through the insertion section and a universal cord.

The integrated coaxial cable 101A extends from an output end of the CIS 100A into the insertion section, further passes through the universal cord, and is removably connected to the processor 4A via a connector provided inside the signal connector.

The integrated coaxial cable 101A is similar to those of the first to third embodiments in that it is a cable connecting the CIS 100A and the processor 4A. In addition to transmission of power supply supplied to the CIS 100A, a video signal (serial signal) on which a synchronization signal transmitted from the CIS 100A is superimposed and a vertical synchronization signal (VD) transmitted from the processor 4A are transmitted and received. Additionally, a two-way communication line 102 connecting the processor 4A and the CIS 100A is held so that communicated contents of multiple control parameters and the like are transmitted and received.

Similarly to the first embodiment, the CIS 100A is provided with a light receiving element 111 arranged at an image forming position of the objective lens 15, an AFE (analog front end) 112 which removes noise from a signal outputted from the light receiving element 111 and digitizes the signal, a synchronization superimposition circuit 113 which superimposes a synchronization signal on a video signal, which is an output signal of the AFE 112, a P/S conversion circuit 114 for converting the video signal to a serial signal for transmission to output the serial signal to an outside, a video signal transmitting section 115 for outputting the video signal (serial signal) to the outside, a synchronization signal receiving section 116 which receives a vertical synchronization signal (VD) and the like from the outside, for example, from the processor 4, a synchronization signal processing section 117 which performs predetermined processing for the synchronization signal from the outside received by the signal receiving section 116 (the vertical synchronization signal (VD) received from the processor 4) in a predetermined case, and a timing generator (TG) 118 which generates its own synchronization signal in the CIS 100A and causing its own synchronization signal to follow the external synchronization signal for which the predetermined processing has been performed by the synchronization signal processing section 117 to supply the synchronization signal to respective circuits as various synchronization signals in the CIS 100A.

Furthermore, the CIS 100A in the fourth embodiment is configured, being provided with a control parameter transmitting/receiving section 141 which receives control parameters transmitted from a control section (FPGA) 200a arranged in the processor 4, a temporary register 142 which temporarily stores the control parameters received by the control parameter transmitting/receiving section 141, and a main register 143 which stores control parameters and the like to be used for photographing control in the CIS 100A.

On the other hand, the processor 4A is provided with: a video signal receiving section 121 which receives a video signal (serial signal) having video data transmitted from the CIS 100A, an S/P conversion circuit 122 which converts the video signal (serial signal) with a synchronization signal superimposed thereon, which has been received by the signal receiving section 121, to a parallel signal, a signal processing section 123 which performs predetermined signal processing for the received video signal and outputs the video signal to the monitor 5 or the like, a timing generator (TG) 125 which generates a vertical synchronization signal (VD) for image processing in the processor 4A and supplies the vertical synchronization signal (VD) to various circuits, and a synchronization signal transmitting section 124 which transmits the vertical synchronization signal (VD) in the processor 4A supplied from the timing generator (TG) 125 to the CIS 100A, similarly to the first embodiment.

Furthermore, the processor 4A is provided with: the control section (FPGA) 200a configured, for example, by an FPGA, a control parameter transmitting/receiving section 211a which transmits multiple control parameters for controlling the CIS 100A, to the CIS 100A via the communication line 102 as well as receiving return data (to be described later in detail) from the CIS 100A, the control parameter transmitting/receiving section 211a being configured in the control section (FPGA) 200a, a judgment section 212a which judges whether or not the multiple control parameters have been normally transmitted from the processor 4A to the CIS 100A, on the basis of the return data from the CIS 100A, a control section 213a which performs predetermined control for treatment and the like of the multiple control parameters transmitted from the processor 4A to the CIS 100A, on the basis of a result of the judgment by the judgment section 212a, and a memory 201 which stores information about the multiple control parameters.

Note that, in the present fourth embodiment also, though the control parameter transmitting/receiving section 211a is assumed to be configured in the control section (FPGA) 200a, another component, the timing generator (TG) 125 may be configured in the FPGA.

In the present fourth embodiment also, the control section (FPGA) 200a reads out various setting values of the multiple control parameters from the memory 201 at the time of startup and transmits the setting values from the control parameter transmitting/receiving section 211a in the control section (FPGA) 200a to the CIS 100A via the integrated coaxial cable 101A, for example, on the basis of the I2C interface. Even after startup, corresponding control parameters are transmitted via communication in order to change settings for a photographing mode, a gain setting, an electronic shutter setting, a cutout position setting and the like as necessary.

Furthermore, though the I2C interface is also adopted as a communication system in the present fourth embodiment, the communication system is not limited thereto, and, for example, the SPI interface may be adopted.

Furthermore, since the kinds and the like of the multiple control parameters transmitted in the image pickup system of the present fourth embodiment are similar to those of the first embodiment, and the multiple control parameters are assumed to be treated as a preset set of integrated information, detailed description thereof is omitted here.

Next, operation in the present embodiment will be described.

In the image pickup system of the present fourth embodiment, at the time of or after startup, the control section (FPGA) 200a reads out various setting values of the multiple control parameters from the memory 201 in the processor 4A and transmits the multiple control parameters from the control parameter transmitting/receiving section 211a to the CIS 100A via the communication line 102 in the integrated coaxial cable 101A.

In comparison, when receiving the multiple control parameters (for example, communicated contents of a gain setting, an electronic shutter setting and a binning setting) transmitted from the control parameter transmitting/receiving section 211a in the control section (FPGA) 200a, the control parameter transmitting/receiving section 141 in the CIS 100A temporarily stores the received contents into the temporary register 142. Note that the contents stored in the temporary register 142 is not reflected on operation of the CIS 100A.

The control parameter transmitting/receiving section 141 transmits the contents of the received multiple control parameters to the control parameter transmitting/receiving section 211a in the processor 4A via the communication line 102 in the integrated coaxial cable 101A. Note that the communicated contents transmitted from the control parameter transmitting/receiving section 141 to the control parameter transmitting/receiving section 211a is called "return data" in the detailed description of the preferred embodiments in the present specification.

Note that, in the present fourth embodiment, a sequence is assumed in which, when receiving the multiple control parameters from the processor 4A, the control parameter transmitting/receiving section 141 temporarily stores the communicated contents into the temporary register 142 as well as immediately transmitting the communicated contents to the control parameter transmitting/receiving section 211a on the processor 4A side as the "return data". However, the sequence is not limited thereto, and a sequence is also possible in which the control parameter transmitting/receiving section 141 temporarily stores the communicated contents into the temporary register 142 and does not start transmission of the return data until receiving a request to transmit the "return data" from the processor 4A.

When receiving the "return data" from the CIS 100A, the control parameter transmitting/receiving section 211a of the processor 4A transmits the "return data" to the judgment section 212a.

The judgment section 212a compares the received "return data" with the "transmitted contents of the multiple control parameters" transmitted from the processor 4A to the CIS 100A previously, and transfers a result of the comparison to the control section 213a.

If the judgment result is OK, the control section 213a does not do anything. On the other hand, if the judgment result is NG, the control section 213a transmits a control signal to the effect that the "transmitted contents of the multiple control parameters" transmitted last should be discarded, to the CIS 100A.

On the other hand, the CIS 100A discards data of the "transmitted contents of the multiple control parameters" stored in the temporary register 142 only in the case of receiving the control signal to the effect that the "transmitted contents of the multiple control parameters" should be discarded.

Note that, though the control signal to the effect that the "transmitted contents of the multiple control parameters" transmitted last should be discarded is transmitted to the CIS 100A if the judgment result is NG, in the present fourth embodiment, the operation is not limited thereto. The control parameter transmitting/receiving section 141 is not necessarily required to explicitly perform the discard operation but is only required to perform such an operation that the communicated contents stored in the temporary register 142 are not reflected on the main register 143.

For example, it is also possible to have a flag indicating whether or not to perform reflection and reflect the data of the temporary register 142 on the main register 143 according to the flag. Otherwise, it is also possible to perform control so that, even if the data is reflected, overwriting with harmless data (for example, contents determined to be reflected last) is performed.

Note that, though transmitted contents of control parameters transmitted from the processor 4A to the CIS 100A and return data from the CIS 100A are compared to judge whether the transmitted contents are correct or incorrect in the fourth embodiment, the judgment is not limited thereto, and it is also possible to transmit and receive an error correcting code (for example, a Hamming code or the like) or an error detecting code (a parity bit, a checksum or the like) together with communicated contents of the multiple control parameters and judge whether the communicated contents are correct or incorrect on the basis of the error correcting code or the error detecting code, similarly to the first to third embodiments.

As described above, according to the fourth embodiment, it is possible to provide an image pickup system in which a CMOS image sensor is arranged at a distal end of an insertion section of an endoscope, and preset multiple control parameters required for photographing control are transmitted from a processor side to a CMOS image sensor side, the image pickup system being capable of always performing normal photographing control by treating the control parameters required for photographing control as a set of integrated information, and performing control so that information about the control parameters is reflected on a register in the CMOS image sensor only when all the multiple control parameters have been normally transmitted and contents of the register are not updated when all the multiple control parameters have not been normally transmitted, similarly to the embodiments described above.

Fifth Embodiment

Next, a fifth embodiment of the present invention will be described.

The image pickup system of the fourth embodiment described above compares "return data" with "transmitted contents of multiple control parameters" transmitted previously, and does not do anything if a result of the comparison is OK. The present fifth embodiment is characterized in that, if the comparison result is OK, a permission to reflect data of the temporary register 142 on the main register 143 is given from the processor 4A to the CIS 100A.

Since the other components, operation and advantages are similar to those of the fourth embodiment, detailed description thereof is omitted here.

Sixth Embodiment

Next, a sixth embodiment of the present invention will be described.

The image pickup system of the fourth embodiment described above is provided with the temporary register 142 and provided with a function as a buffer which temporarily holds multiple control parameters received from the CIS 100A. The present sixth embodiment is different from the fourth embodiment in that a function corresponding to the temporary register 142 which temporarily holds data is not provided.

Note that only parts different from the fourth embodiment will be described here, and description of components similar to those of the fourth embodiments is omitted.

Figure 8:
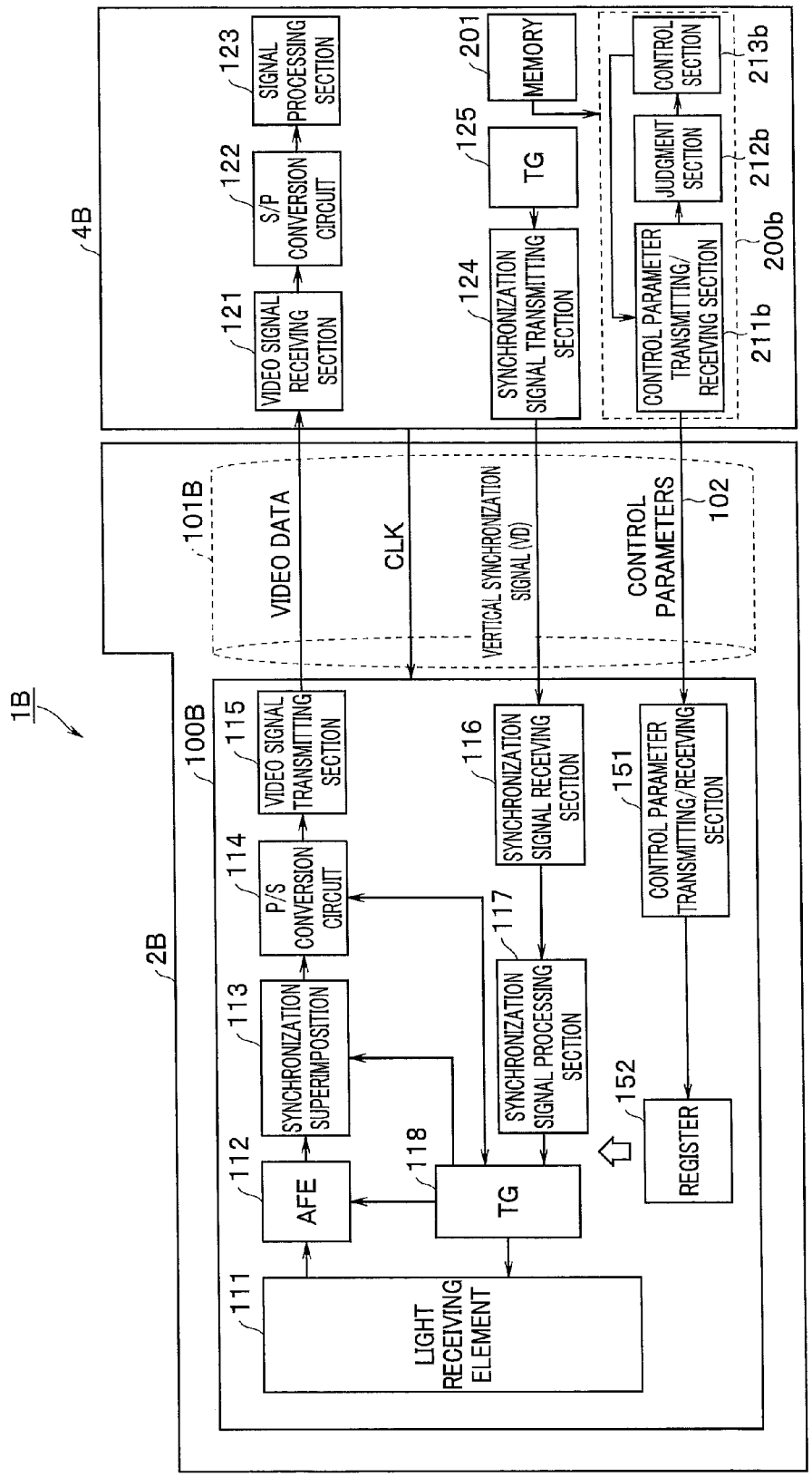
FIG. 8 is a diagram showing a configuration of an electric system in an image pickup system of a sixth embodiment of the present invention.

FIG. 8 is a block diagram showing a configuration of an electric system in an image pickup system of the sixth embodiment of the present invention.

As shown in FIG. 8, an image pickup system 1B provided with an image pickup apparatus according to the sixth embodiment of the present invention is provided with: an endoscope 2B provided with an image pickup device (CIS) 100B, a light source apparatus to which the endoscope 2B is removably connected and which supplies an illumination light to the endoscope 2B, a processor 4B as a signal processing apparatus to which the endoscope 2B is removably connected and which performs predetermined signal processing, and a monitor as a display apparatus which displays an image signal generated by the processor 4B as an endoscopic image.

Similarly to the first embodiment, the image pickup device (CIS) 100B in the image pickup system 1B of the sixth embodiment is configured by a so-called CMOS (complementary metal oxide semiconductor circuit) image sensor arranged at a distal end of an insertion section and connected to the processor 4B via an integrated coaxial cable 101B inserted through the insertion section and a universal cord.

Similarly to the first and fourth embodiments, the CIS 100B is provided with a light receiving element 111 arranged at an image forming position of the objective lens 15, an AFE (analog front end) 112 which removes noise from a signal outputted from the light receiving element 111 and digitizes the signal, a synchronization superimposition circuit 113 which superimposes a synchronization signal on a video signal, which is an output signal of the AFE 112, a P/S conversion circuit 114 for converting the video signal to a serial signal for transmission to output the serial signal to an outside, a video signal transmitting section 115 for outputting the video signal (serial signal) to the outside, a synchronization signal receiving section 116 which receives a vertical synchronization signal (VD) and the like from the outside, for example, from the processor 4B, a synchronization signal processing section 117 which performs predetermined processing for the synchronization signal from the outside received by the synchronization signal receiving section 116 (the vertical synchronization signal (VD) received from the processor 4B) in a predetermined case, and a timing generator (TG) 118 which generates its own synchronization signal in the CIS 100B and causing its own synchronization signal to follow the external synchronization signal for which the predetermined processing has been performed by the synchronization signal processing section 117 to supply the synchronization signal to respective circuits as various synchronization signals in the CIS 100A.

Furthermore, the CIS 100B in the sixth embodiment is configured, being provided with a control parameter transmitting/receiving section 151 which receives control parameters transmitted from a control section (FPGA) 200b arranged in the processor 4B, and a register 152 which stores the control parameters received by the control parameter transmitting/receiving section 151 as control parameters to be used for photographing control in the CIS 100B.

On the other hand, the processor 4B is provided with: a video signal receiving section 121 which receives a video signal (serial signal) having video data transmitted from the CIS 100B, an S/P conversion circuit 122 which converts the video signal (serial signal) with a synchronization signal superimposed thereon, which has been received by the signal receiving section 121, to a parallel signal, a signal processing section 123 which performs predetermined signal processing for the received video signal and outputs the video signal to the monitor 5 or the like, a timing generator (TG) 125 which generates a vertical synchronization signal (VD) for image processing in the processor 4B and supplies the vertical synchronization signal (VD) to various circuits, and a synchronization signal transmitting section 124 which transmits the vertical synchronization signal (VD) in the processor 4B supplied from the timing generator (TG) 125 to the CIS 100B, similarly to the fourth embodiment.

Furthermore, the processor 4B is provided with: the control section (FPGA) 200b configured, for example, by an FPGA, a control parameter transmitting/receiving section 211b which transmits multiple control parameters for controlling the CIS 100B, to the CIS 100B via the communication line 102 as well as receiving return data from the CIS 100B, the control parameter transmitting/receiving section 211b being configured in the control section (FPGA) 200b, a judgment section 212b which judges whether or not the multiple control parameters have been normally transmitted from the processor 4B to the CIS 100B, on the basis of the return data from the CIS 100B, a control section 213b which performs predetermined control for treatment and the like of the multiple control parameters transmitted from the processor 4B to the CIS 100B, on the basis of a result of the judgment by the judgment section 212b, and a memory 201 which stores information about the multiple control parameters.

Next, operation in the present embodiment will be described.

In the image pickup system of the present sixth embodiment, at the time of or after startup, the control section (FPGA) 200b reads out various setting values of the multiple control parameters from the memory 201 in the processor 4A and transmits the multiple control parameters from the control parameter transmitting/receiving section 211b to the CIS 101B via the communication line 102 in the integrated coaxial cable 101B.

In comparison, when receiving the multiple control parameters transmitted from the control parameter transmitting/receiving section 211b in the control section (FPGA) 200b, the control parameter transmitting/receiving section 151 in the CIS 100B immediately reflects contents of the received multiple control parameters on the register 152 as well as transmitting the contents to the control parameter transmitting/receiving section 211b in the processor 4B via the communication line 102 in the integrated coaxial cable 101B as return data.

When receiving the "return data" from the CIS 100B, the control parameter transmitting/receiving section 211b of the processor 4B transmits the "return data" to the judgment section 212b.

The judgment section 212b compares the received "return data" with the "transmitted contents of the multiple control parameters" transmitted from the processor 4B to the CIS 100B previously, and transfers a result of the comparison to the control section 213b.

If the judgment result is NG, the control section 213b transmits "multiple control parameters" with the same contents as the "transmitted contents of the multiple control parameters" transmitted last, to the CIS 100B.

Note that, though transmitted contents of control parameters transmitted from the processor 4B to the CIS 100B and return data from the CIS 100B are compared to judge whether the transmitted contents are correct or incorrect in the sixth embodiment also, the judgment is not limited thereto, and it is also possible to transmit and receive an error correcting code (for example, a Hamming code or the like) or an error detecting code (a parity bit, a checksum or the like) together with communicated contents of the multiple control parameters and judge whether the communicated contents are correct or incorrect on the basis of the error correcting code or the error detecting code, similarly to the first to fourth embodiments.

As described above, according to the sixth embodiment, it is possible to provide an image pickup system in which a CMOS image sensor is arranged at a distal end of an insertion section of an endoscope, and preset multiple control parameters required for photographing control are transmitted from a processor side to a CMOS image sensor side, the image pickup system being capable of always performing normal photographing control by treating the control parameters required for photographing control as a set of integrated information, and performing control so that information about the control parameters is reflected on a register in the CMOS image sensor only when all the multiple control parameters have been normally transmitted and contents of the register are not updated when all the multiple control parameters have not been normally transmitted, similarly to the embodiments described above.

Seventh Embodiment

Next, a seventh embodiment of the present invention will be described.

The image pickup system of the sixth embodiment described above compares "return data" with "transmitted contents of multiple control parameters" transmitted previously, and, if a result of the comparison is NG, transmits "multiple control parameters" with the same contents as the "transmitted contents of the multiple control parameters" transmitted last to the CIS 100B. The present seventh embodiment is characterized in that, if the comparison result is NG, an instruction to discard the "transmitted contents of the multiple control parameters transmitted last" currently stored in the register 152 and return the contents to contents before the contents is transmitted from the processor 4B to the CIS 100B.

Since the other components, operation and advantages are similar to those of the sixth embodiment, detailed description thereof is omitted here.

Eighth Embodiment

Next, an eighth embodiment of the present invention will be described.

Figure 9:
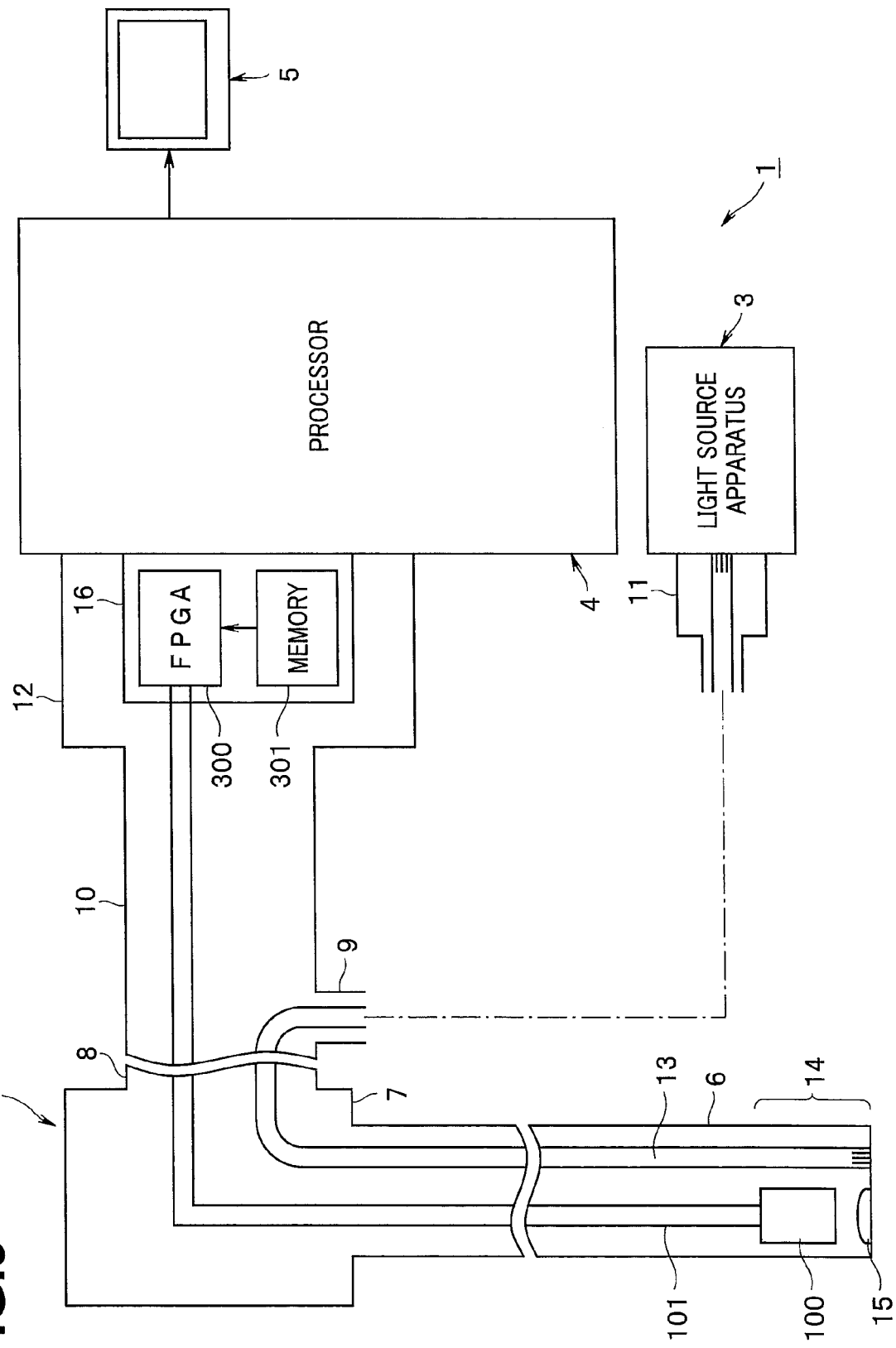
FIG. 9 is a diagram showing a whole configuration of an image pickup system of an eighth embodiment of the present invention.

FIG. 9 is a diagram showing a whole configuration of an image pickup system of the eighth embodiment of the present invention.

The image pickup systems of the first to seventh embodiments described above are configured such that both of the control section (FPGA) 200 (200a, 200b) and the memory 201 are provided in the processor 4 (4A, 4B). The present eighth embodiment is characterized in that both of a control section (FPGA) 300 and a memory 301 corresponding to the control section (FPGA) 200 (200a, 200b) and the memory 201, respectively, are provided in the connector 16 on the endoscope 2 side.

Since the other components, operation and advantages are similar to the first to seventh embodiments, detailed description thereof is omitted here.

An object of the image pickup system of the invention as claimed in the application concerned is to provide an image pickup system capable of accurately transmitting necessary multiple control parameters, coping with disorder of a transmitted signal due to disturbance influencing a connection cable between a CIS arranged at a distal end of an insertion section of an endoscope and a control section (FPGA) arranged at a position at a relatively long distance from the CIS, and capable of always performing normal photographing control. In addition to the case where the control section (FPGA) communicating with the CIS is arranged in a processor, this problem also applies to the case where the control section (FPGA) is arranged at a connector connecting the endoscope and the processor like the present embodiment.

In the image pickup system of the present eighth embodiment, by the CIS 100, the control section (FPGA) 300 which communicates with the CIS 100 and the memory 301 which stores information about multiple control parameters having configurations similar to those of the CIS 100 (100A, 100B), the control section (FPGA) 200 (200a, 200b) and the memory 201, respectively, operation and advantages similar to those of the first to seventh embodiments described above are obtained.

Ninth Embodiment

Next, a ninth embodiment of the present invention will be described.

Figure 10:
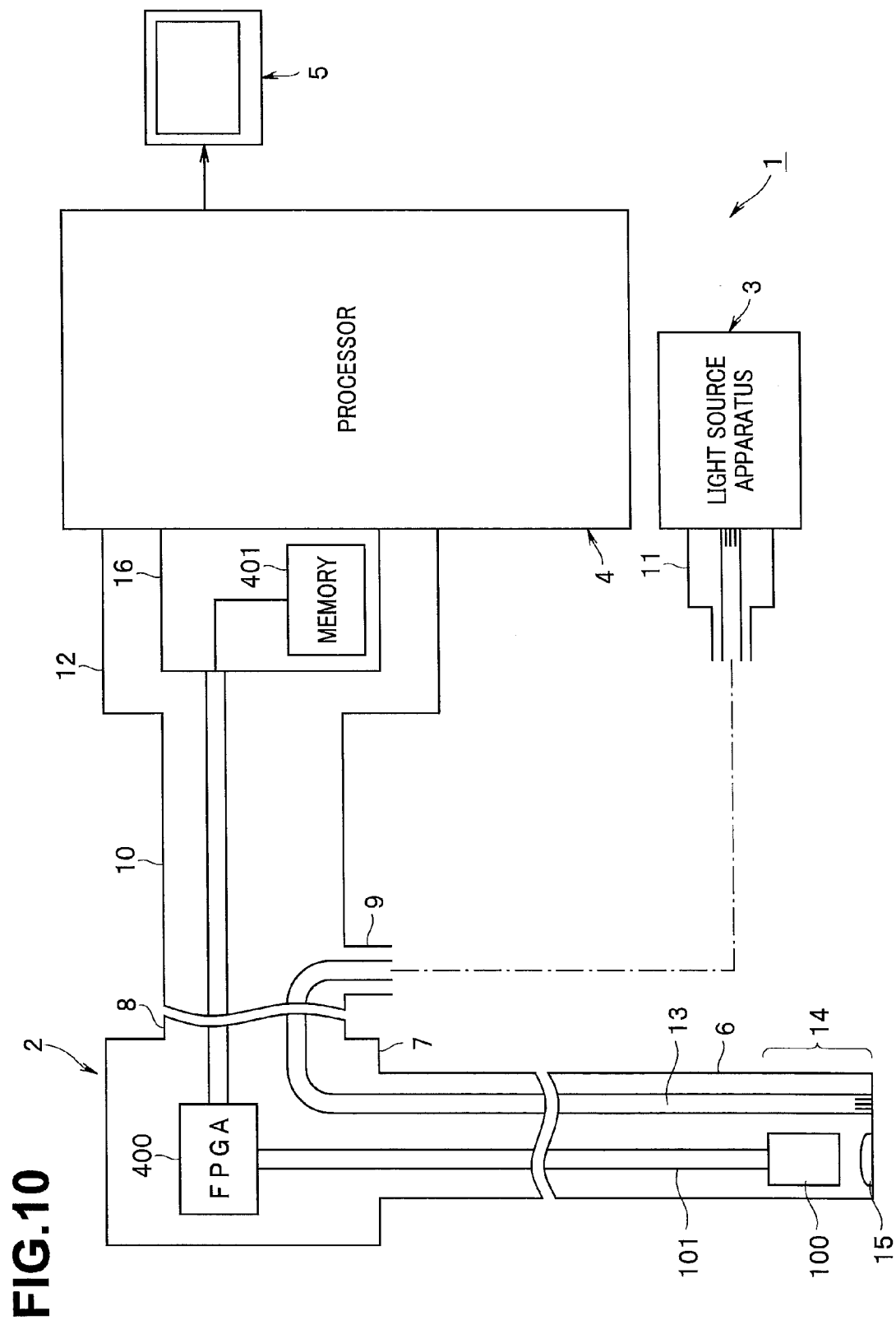
FIG. 10 is a diagram showing a whole configuration of an image pickup system of a ninth embodiment of the present invention.

FIG. 10 is a diagram showing a whole configuration of an image pickup system of the ninth embodiment of the present invention.

The present ninth embodiment is characterized in that a control section (FPGA) 400 and a memory 401 corresponding to the control section (FPGA) 200 (200a, 200b) and the memory 201 are arranged in an operation section 7 of an endoscope 2 and in the connector 16 on the endoscope 2 side, respectively, similarly to the eighth embodiment described above.

In the ninth embodiment also, by a CIS 100, the control section (FPGA) 400 which communicates with the CIS 100 and the memory 401 which stores information about multiple control parameters having configurations similar to those of the CIS 100 (100A, 100B), the control section (FPGA) 200 (200a, 200b) and the memory 201 in the first to seventh embodiments described above, respectively, operation and advantages similar to those of the first to seventh embodiments described above are obtained, similarly to the eighth embodiment described above.

Tenth Embodiment

Next, a tenth embodiment of the present invention will be described.

Figure 11:
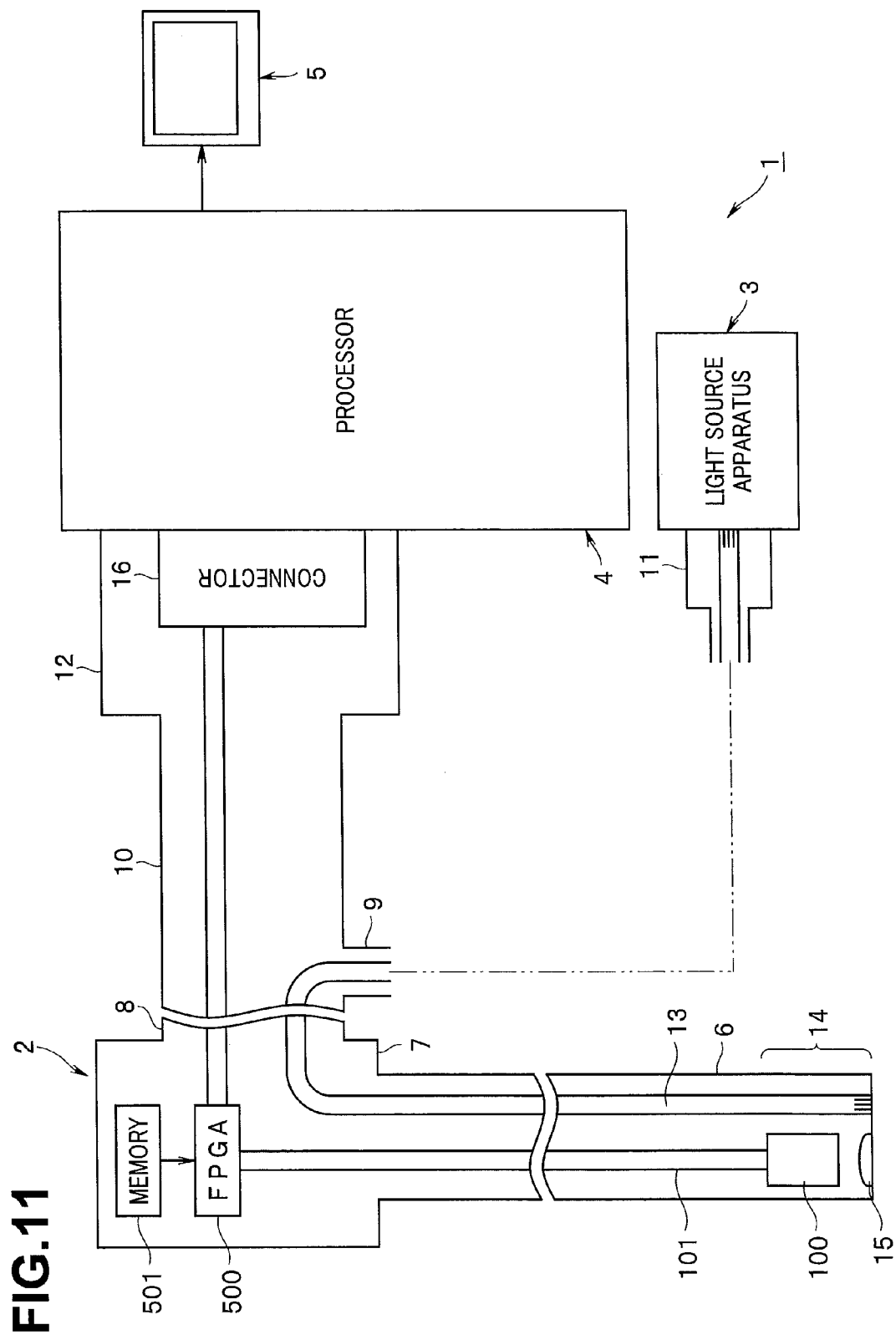
FIG. 11 is a diagram showing a whole configuration of an image pickup system of a tenth embodiment of the present invention.

FIG. 11 is a diagram showing a whole configuration of an image pickup system of the tenth embodiment of the present invention.

The present tenth embodiment is characterized in that both of a control section (FPGA) 500 and a memory 501 corresponding to the control section (FPGA) 200 (200a, 200b) and the memory 201, respectively, are arranged in an operation section 7 of an endoscope 2, similarly to the eighth and ninth embodiments described above.

The tenth embodiment is also similar to the embodiments described above in that the CIS 100 and the control section (FPGA) which communicates with the CIS 100 are separated from each other by a relatively long distance. Therefore, similarly to the eighth and ninth embodiments, by the CIS 100, the control section (FPGA) 500 which communicates with the CIS 100 and the memory 501 which stores information about multiple control parameters having configurations similar to those of the CIS 100 (100A, 100B), the control section (FPGA) 200 (200a, 200b) and the memory 201 in the first to seventh embodiment described above, respectively, operation and advantages similar to those of the first to seventh embodiments described above, operations and advantages similar to those of the first to seventh embodiments described above are obtained.

Note that, though an image pickup system provided with a CMOS image sensor as an image pickup device which is arranged at a distal end of an insertion section of an endoscope to pick up an image of an object and which is provided with a function of having a register for storing control parameters and the like for photographing control is given as an example, the present invention is not limited thereto and is also applicable to an image pickup system provided with an endoscope with a so-called CCD arranged at the distal end of an insertion section thereof and with a register for storing control parameters and the like to be used for photographing control arranged near the CCD.

Note that the present invention is not immediately limited to each embodiment described above, and components can be modified and embodied at an implementation stage within a range not departing from the spirit of the present invention. Various inventions can be formed by appropriate combination of the multiple components disclosed in each embodiment described above. For example, some components among all the components shown in the embodiments may be deleted. Furthermore, components among different embodiments may be appropriately combined.

What is claimed is:

1. An image pickup system comprising:
   an image pickup apparatus generating and outputting an image signal by receiving a light and performing photoelectric conversion;
   a control apparatus sending out control parameters for performing drive control of the image pickup apparatus, wherein the image pickup apparatus and the control apparatus are capable of communicating with each other,
   the image pickup system further comprising:
   a first communication section being provided in the control apparatus and transmitting multiple control parameters for controlling photographing of the image pickup apparatus to the image pickup apparatus;
   a second communication section being provided in the image pickup apparatus, the second communication section receiving the multiple control parameters transmitted from the first communication section, storing the received multiple control parameters in a temporary register, and transmitting the received multiple control parameters to the first communication section;
   a judgment section being provided in the control apparatus and judging, in the control apparatus, after receiving the multiple parameters by the second communication section, whether all of the multiple control parameters transmitted from the first communication section in the control apparatus to the second communication section are normally transmitted, by comparing the multiple control parameters transmitted by the first communication section with the multiple control parameters received by the first communication section;

a control-apparatus-side control section being provided in the control apparatus and transmitting, when judging that all of the multiple control parameters received by the image pickup apparatus are normally transmitted on the basis of a result of the judgment by the judgment section, a control signal permitting the image pickup apparatus to reflect the multiple control parameters related to the judgment result, to the image pickup apparatus via the first communication section; and a photographing control section being provided in the image pickup apparatus and causing the multiple control parameters stored in the temporary register to be stored in a main register and reflected on photographic control, on the basis of the result of the judgment by the judgment section.

2. The image pickup system according to claim 1, wherein the first communication section transmits the multiple control parameters for controlling photographing of the image pickup apparatus to the image pickup apparatus as well as transmitting an error detecting code or an error correcting code used when judging or correcting an error of the multiple control parameters;

the second communication section receives the control parameters and the error detecting code or the error correcting code transmitted from the first communication section; and the judgment section judges whether the multiple control parameters received by the second communication section are normally transmitted or not on the basis of the error detecting code or the error correcting code transmitted by the control apparatus.

3. The image pickup system according to claim 2, wherein, when judging that all the multiple control parameters, which are a preset set, received by the second communication section have been received without an error, the judgment section judges that the multiple control parameters received by the second communication section are normally transmitted.

4. The image pickup system according to claim 2, wherein, when judging that the multiple control parameters received by the second communication section are not normally transmitted on the basis of the result of the judgment by the judgment section, the photographing control section does not reflect information about the received control parameters.

5. The image pickup system according to claim 2, wherein, when judging that the multiple control parameters received by the second communication section are not normally transmitted on the basis of the result of the judgment by the judgment section, the photographing control section stores the communication result.

6. The image pickup system according to claim 2, wherein the judgment section is provided in the image pickup apparatus.

7. The image pickup system according to claim 1, wherein the first communication section is capable of transmitting and receiving data to and from the image pickup apparatus, transmits the multiple control parameters for controlling photographing of the image pickup apparatus to the image pickup apparatus, and further receives communicated information about the multiple control parameters from the image pickup apparatus;

the judgment section judges whether the multiple control parameters received by the image pickup apparatus are normally transmitted or not on the basis of the communicated information about the multiple control parameters from the image pickup apparatus;

the second communication section of the image pickup apparatus is capable of transmitting and receiving data to and from the control apparatus, receives the multiple control parameters transmitted from the first communication section as well as transmitting the communicated information about the received multiple parameters to the control apparatus; and the image pickup apparatus comprises the photographing control section for performing photographing control by the multiple control parameters received by the second communication section, on the basis of the result of the judgment by the judgment section.

8. The image pickup system according to claim 7, wherein the first communication section further transmits a data transmission requesting signal requesting the image pickup apparatus to transmit the communicated information about the multiple control parameters from the image pickup apparatus, to the image pickup apparatus; and the second communication section transmits the communicated information about the multiple control parameters to the control apparatus in response to the data transmission requesting signal.

9. The image pickup system according to claim 7, wherein the control-apparatus-side control section transmits the control signal only when judging that the multiple control parameters received by the image pickup apparatus are not normally transmitted on the basis of the result of the judgment by the judgment section; and the photographing control section performs photographing control on the basis of the control signal.

10. The image pickup system according to claim 7, wherein the photographing control section performs photographing control without reflecting the multiple control parameters related to the judgment result, on the basis of the control signal.

11. The image pickup system according to claim 1, wherein when judging that even one of the multiple parameters received by the image pickup apparatus is not normally transmitted on the basis of the judgment result by the judgment section, the control-apparatus side control section transmits a control signal not permitting the image pickup apparatus to reflect any of the multiple control parameters related to the judgment result, to the image pickup apparatus via the first communication section.

12. The image pickup system according to claim 1, wherein all of the parameters mean all control parameters in a group of control parameters constituted of some control parameters among the multiple control parameters.

* * * * *